US00PP36841P2

(12) United States Plant Patent
Jury

(10) Patent No.: US PP36,841 P2
(45) Date of Patent: Jul. 22, 2025

(54) ***MAGNOLIA* PLANT NAMED 'MicJur12'**

(50) Latin Name: ***Magnolia yunnanensis* x *figo***
Varietal Denomination: MicJur12

(71) Applicant: Mark Jury, Waitara (NZ)

(72) Inventor: Mark Jury, Waitara (NZ)

( * ) Notice: Subject to any disclaimer, the term of this patent is extended or adjusted under 35 U.S.C. 154(b) by 0 days.

(21) Appl. No.: 18/944,056

(22) Filed: Nov. 12, 2024

(51) Int. Cl.
*A01H 5/02* (2018.01)
*A01H 5/00* (2018.01)

(52) U.S. Cl.
USPC ..... Plt./223

(58) Field of Classification Search
USPC ..... Plt./223
See application file for complete search history.

*Primary Examiner* — Shubo (Joe) Zhou
*Assistant Examiner* — Zachariah Allan Kay
(74) *Attorney, Agent, or Firm* — Cassandra Bright

(57) ABSTRACT

A new and distinct *Magnolia* cultivar named 'MicJur12' is disclosed, characterized by dense, compact growth and highly floriferous plants. Flowers produced by the new cultivar are small and uniquely colored yellow with a red-purple flush. Plants are sun tolerant and do not scorch or wilt in direct sunlight. The new variety is a *Magnolia*, normally produced as a small ornamental tree or shrub.

2 Drawing Sheets

Figure 1:
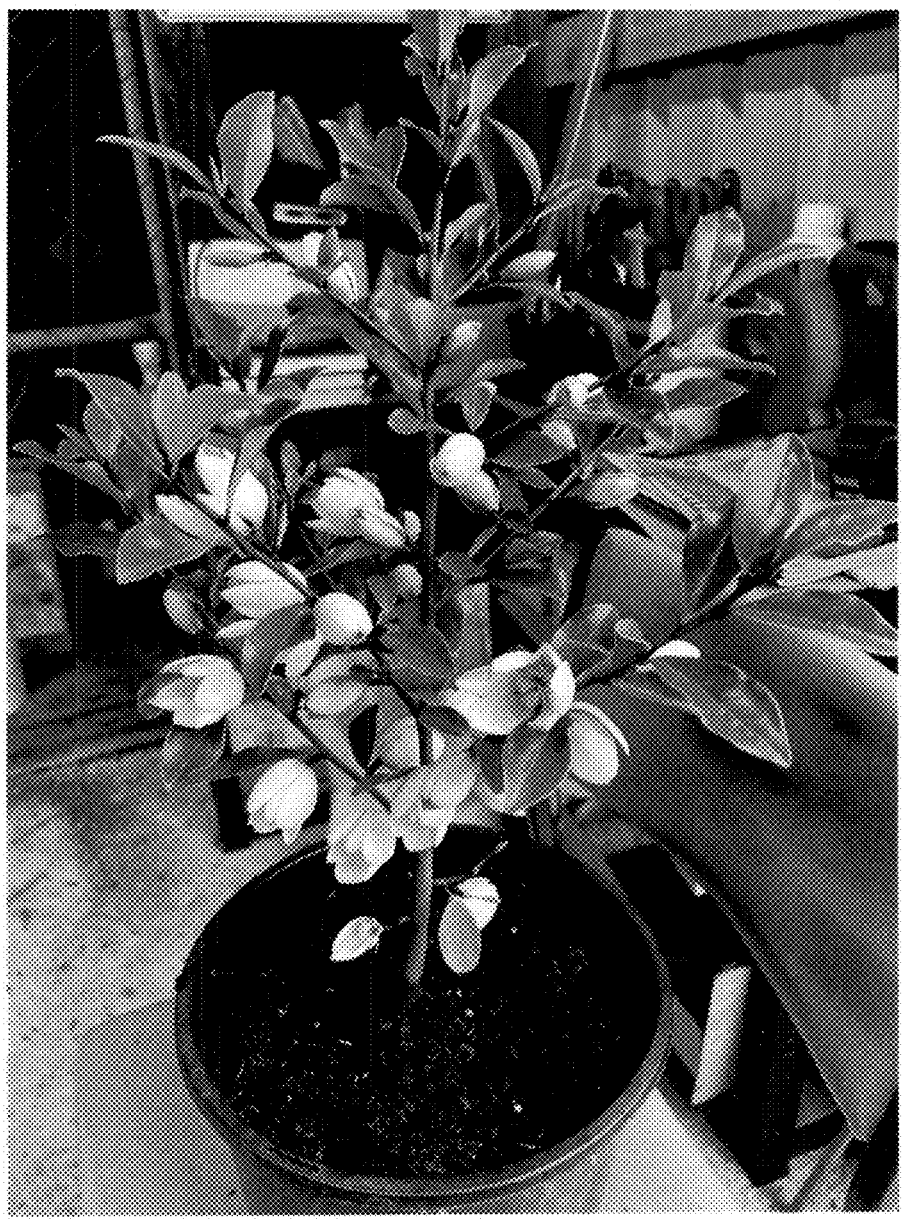

Latin name of the genus and species: *Magnolia yunnanensis* x *figo*.
Variety denomination: 'MicJur12'.

BACKGROUND OF THE INVENTION

The new cultivar is a product of a planned breeding program. The new variety resulted from a crossing performed in 1995 in North Taranaki, New Zealand. The seed parent is the unpatented variety, *Magnolia yunnanensis* 'Velvet and Cream'. The pollen parent is an unnamed, *Magnolia figo*. The new variety was selected for further testing in 2000 by the inventor, Mark Jury at a commercial nursery in North Taranaki, New Zealand.

Asexual reproduction of the new cultivar 'MicJur12' was first in performed in 2000, using semi-softwood cuttings, at a commercial nursery in New Zealand. This and subsequent propagation have shown that the unique features of this cultivar are stable and reproduced true to type on successive generations.

SUMMARY OF THE INVENTION

The cultivar 'MicJur12' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MicJur12'. These characteristics in combination distinguish 'MicJur12' as a new and distinct *Magnolia* cultivar:

1. Compact growth.
2. Highly floriferous plants.
3. Unique flower color; yellow with a red-purple flush.
4. Plants are sun tolerant. Flowers and foliage do not scorch or wilt in direct sunlight.

PARENT COMPARISON

Plants of the new cultivar 'MicJur12' are similar to plants of the seed parent, *Magnolia yunnanensis* 'Velvet and Cream' in most horticultural characteristics, however, plants of the new cultivar 'MicJur12' more compact and denser. Flowers of the new variety are lemon yellow with a red-purple flush; flowers of the seed parent are white.

Plants of the new cultivar 'MicJur12' are similar to plants of the pollen parent, *Magnolia figo* in most horticultural characteristics. However, plants of the new cultivar are more compact and denser. Additionally, the new variety is much more floriferous than the pollen parent. Plants of the pollen parent produce smaller, less colorful flowers and softer foliage than 'MicJur12'.

COMMERCIAL COMPARISON

Plants of the new cultivar 'MicJur12' are similar to plants of the commercial cultivar, *Magnolia* 'MICJUR01', U.S. Plant Pat. No. 21,873 in most horticultural characteristics. However, plants of the new cultivar differ in the following characteristics:

1. 'MicJur12' has smaller flowers at 3.5 cm in diameter; flowers of 'MicJur01' are typically 6 cm in diameter.
2. 'MicJur12' has flowers colored lemon yellow and flushed red-purple for an overall lemon yellow/peach appearance. Flowers of 'MicJur01' are light pink.
3. Plants of 'MicJur12' are smaller than plants of 'MicJur01'.

Plants of the new cultivar 'MicJur12' are similar to plants of the commercial cultivar, *Magnolia* 'MICJUR02', U.S. Plant Pat. No. 25,850 in most horticultural characteristics. However, plants of the new cultivar differ in the following characteristics:

1. 'MicJur12' has smaller flowers at 3.5 cm in diameter; flowers of MicJur02' are typically 10 to 12 cm in diameter.
2. 'MicJur12' has flowers colored lemon yellow and flushed red-purple for an overall lemon yellow/peach appearance. Flowers of 'MicJur02' are white with a yellow-green flush.

3. Plants of 'MicJur12' are smaller than plants of 'MicJur02'.

BRIEF DESCRIPTION OF THE PHOTOGRAPHS

The accompanying photograph in FIG. 1 illustrates in full color a typical plant of 'MicJur12' grown outdoors in North Taranaki, New Zealand. Age of the plant photographed is approximately 3 years.

Figure 2:
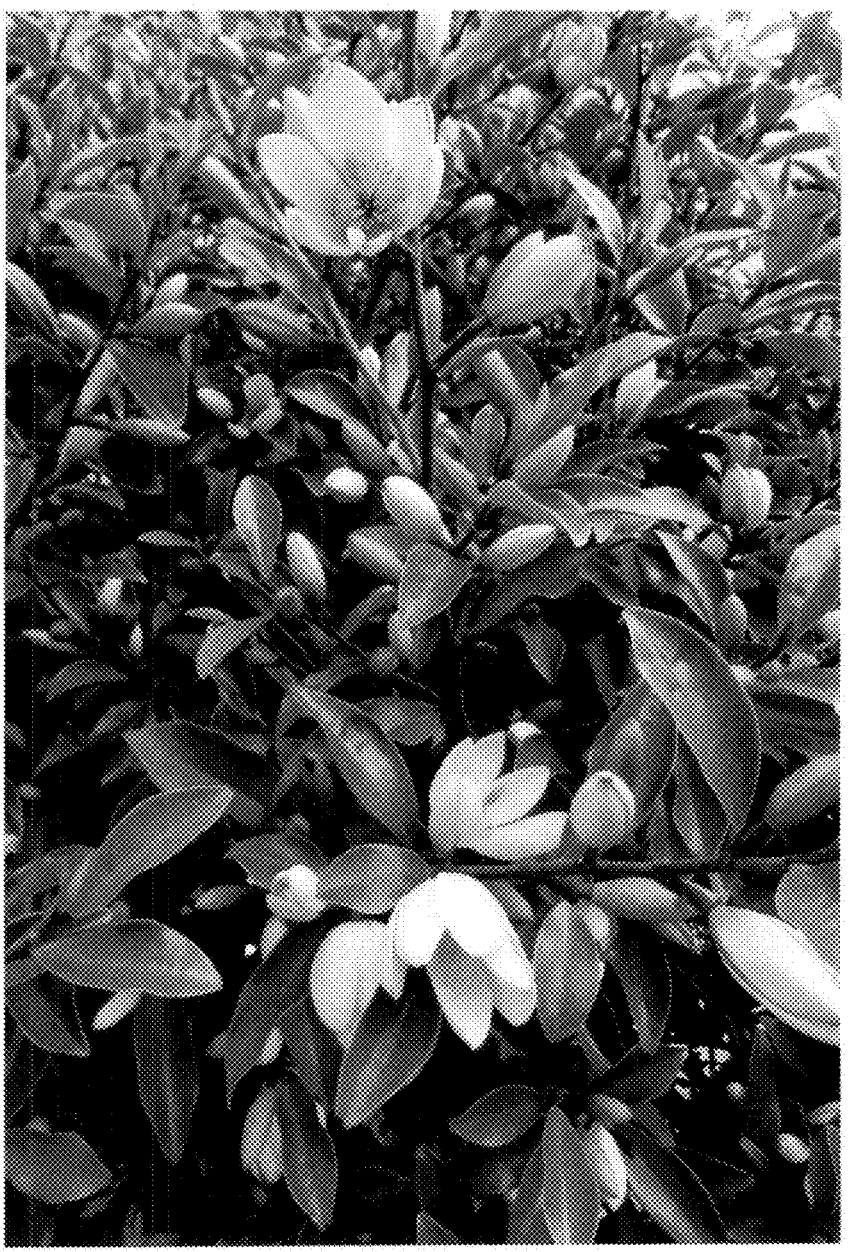

FIG. 2 illustrates in full color typical flowers of 'MicJur12'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'MicJur12' plants grown outdoors in North Taranaki, New Zealand. Growing conditions are similar to USDA Zone 7. Age of the plants when described is approximately 3 years old. Measurements and numerical values represent averages of typical plant types.

Botanical classification: *Magnolia yunnanensis* x *figo* 'MicJur12'.

PROPAGATION

Time to initiate roots: About 60 days at approximately 21° C.

Time to produce a rooted cutting: About 120 days at 21° C.

Root description: Typical *Magnolia* root, thick, coarse, colored near RHS White 155A.

PLANT

Growth habit: Bushy, dense evergreen small tree.

Mature height: Approximately 150 to 250 cm at 3 years.

Mature spread: Approximately 150 cm at 3 years.

Stem diameter: Approximately 6 cm at 3 years.

Branching characteristics: Depends upon cultural techniques. Without pruning, a Normally a single trunk tree with lateral branches forming at acute angles to the trunk. With pruning, plants can be grown as large shrubs.

Individual branch characteristics (of 1 year old tree):

*Length*.—Up to 25 cm.

*Diameter*.—Up to.5 cm.

*Texture*.—Smooth.

*Color*.—Near RHS 197D.

Trunk:

*Diameter*.—Approximately 15 cm, after 12 years. Measured approximately 10 cm above the ground.

*Texture*.—Smooth.

*Color*.—Near RHS 197D.

FOLIAGE

Leaf:

*Arrangement*.—Mixed: opposite, and occasionally alternate.

*Average length*.—Approximately 6 to 7 cm.

*Average width*.—Approximately 3 cm.

*Shape of blade*.—Elliptic.

*Apex*.—Acute.

*Base*.—Attenuate.

*Margin*.—Entire.

*Texture of top surface*.—Smooth, with glossy appearance.

*Texture of lower surface*.—Smooth.

*Leaf internode length*.—Approximately 1.5 cm.

*Color*.—Mature foliage upper side: Near RHS Yellow-Green 137A. Mature foliage under side: Near RHS Yellow-Green 137D.

*Venation*.—Type: Pinnate. Venation color upper side: Near RHS Yellow-Green 144C. Venation color under side: Near RHS Yellow-Green 144B.

*Petiole*.—Not present, sessile.

FLOWER

Natural flowering season: Flowering begins in early Spring. Lasts approximately 4 to 6 weeks.

Begins flowering after how many years/months: 1.5 to 2 years after planting an unrooted cutting.

Inflorescence type and habit: Solitary occurring, rotate. Flowers have a flattened aspect in the upper profile, and flattened convex aspect in the lower profile.

Individual flower size:

*Diameter*.—Average 3.5 cm.

*Depth*.—Approximately 4 cm.

Peduncle:

*Length*.—Average range 5 to 9 mm.

*Diameter*.—Average 5 mm.

*Color*.—Near RHS Yellow-Green 148A.

*Texture*.—Soft velvety pubescence.

Pedicel: Not present.

Tepals:

*Quantity*.—6.

*Petal arrangement*.—Rotate, slightly overlapping.

*Shape*.—Elliptic.

*Size*.—Length.—3.5 cm. Width: 1.5 cm.

*Margin*.—Entire.

*Apex*.—Acute.

*Base*.—Rounded.

*Texture*.—Smooth, all surfaces.

Color:

*Petals*.—When opening: Upper surface: Near RHS Yellow 5D, flushed Red-Purple N74A. Lower surface: Near RHS Yellow 5D, flushed Red-Purple N74A. Fully opened: Upper surface: Near RHS Yellow 5D, marginal flush Red-Purple N74A. Basal spot N74A. Lower surface: Near RHS Yellow 5D, marginal flush Red-Purple N74A.

Bud:

*Shape*.—Ovate.

*Length*.—Approximately 2 cm.

*Diameter*.—Approximately 1 cm.

*Color*.—Near RHS Yellow 5D, flushed Red-Purple N74A.

Sepals/tepals: Not Present.

Fragrance: None.

Duration of the bloom: Typically about 2 weeks.

REPRODUCTIVE ORGANS

Stamens:

*Number*.—Approximately 25.

*Filament length*.—Approximately 1 cm.

*Filament color*.—Near RHS Yellow 11D.

Anthers:

*Length*.—Approximately 1 mm.

*Shape*.—Linear.

*Color*.—Near RHS Red-Purple N74A.

Pistil:

*Number*.—1.

*Length*.—Approximately 8 mm.

*Style*.—Length: Approximately 7 mm. Color: Near RHS Yellow-Green 144B.

*Pollen*.—Quantity: Moderate. Color: Near RHS Red-Purple N74A.

OTHER CHARACTERISTICS

Seeds and fruits: No fruit observed to date, the inventor does not expect the new variety to set fruit.

Disease/pest resistance: Neither resistance nor susceptibility to pathogens and pests common to *Magnolia* have been observed.

Temperature tolerance: The new variety is suitable for growing in USDA zones 7 through 11.

What is claimed is:

1. A new and distinct cultivar of *Magnolia* plant named 'MicJur12' as herein illustrated and described.

* * * * *